United States Patent [19]
Bennett et al.

[11] 3,975,521
[45] Aug. 17, 1976

[54] PROSTATE CARCINOMA TREATMENT

[75] Inventors: Donald R. Bennett, Midland, Mich.; James A. McHard, Gainesville, Fla.

[73] Assignee: Dow Corning Corporation, Midland, Mich.

[22] Filed: May 1, 1974

[21] Appl. No.: 465,780

Related U.S. Application Data

[63] Continuation-in-part of Ser. No. 837,922, June 30, 1969, Pat. No. 3,830,912, which is a continuation-in-part of Ser. No. 741,336, July 1, 1968, abandoned.

[52] U.S. Cl. ............................................. 424/184
[51] Int. Cl.² ..................................... A61K 31/695

[58] Field of Search .................................... 424/184

[56] References Cited
UNITED STATES PATENTS

| | | | |
|---|---|---|---|
| 2,934,472 | 4/1960 | May | 424/184 |
| 3,382,150 | 5/1968 | Grass et al. | 424/184 |

*Primary Examiner*—Jerome D. Goldberg
*Attorney, Agent, or Firm*—Norman E. Lewis

[57] ABSTRACT

Patients suffering from prostate carcinoma obtain a palliative action upon administration of 2,6-cis-diphenylhexamethylcyclotetrasiloxane.

5 Claims, No Drawings

PROSTATE CARCINOMA TREATMENT

This application is a continuation-in-part of our copending application Ser. No. 837,922, filed June 30, 1969, now U.S. Pat. No. 3,830,912, which in turn is a continuation-in-part of application Ser. No. 741,336, filed July 1, 1968; now abandoned.

The present invention relates to a method of treating prostate carcinoma. Specifically, the invention provides a method producing palliative action in the treatment of prostate carcinoma comprising administering an effective amount of 2,6-cis-diphenylhexamethylcyclotetrasiloxane to a patient suffering from the disease.

The siloxane used in the practice of the present invention can be named as 2,6-cis-diphenyl-2,4,4,6,8,8-hexamethylcyclotetrasiloxane and is of the formula

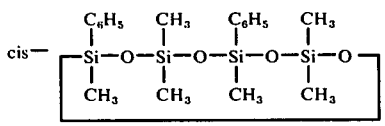

The cyclotetrasiloxane and a method of its preparation are disclosed in U.S. Pat. No. 3,652,628.

The organosilicon compound can be administered orally in combination with a pharmaceutically acceptable carrier or diluent. Suitable carriers include sesame oil, corn oil, mineral oil, soya oil, oleic acid and other well-known fat soluble vehicles or emulsions conventionally employed in numerous pharmaceutical preparations. Other compounds, for example the trans isomer of 2,6-diphenylhexamethylcyclotetrasiloxane, may also be present in small amounts. It is also within the scope of the present invention to parenterally administer the organosilicon compound, such as by subcutaneous or intramuscular administration. The effective dosage to obtain palliative relief of prostate carcinoma appears to be in the range of 1 to 50 mg./kilogram of body weight on a daily basis. The practice of the method is not to be limited to the values since the effective amount can vary substantially in individual cases, depending especially upon the stage of advancement of the disease.

It is to be emphasized that treatment in accordance with the present invention does not affect a cure of prostate carcinoma, but does provide palliative relief and alleviates some of the symptoms of the disease. Practice of the present method is especially useful in providing relief of analgesic-resistant pain in patients suffering from the advanced stages of prostate carcinoma. The organosilicon compound does possess antigonadotropic activity and it is believed that this activity provides the palliative action in the treatment of prostate carcinoma.

EXAMPLE 1

Dimethyldichlorosilane and a meso/racemic compound of the formula

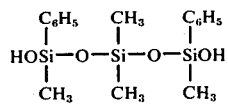

were reacted in accordance with the method described in Example 2 of U.S. Pat. No. 3,652,628 to obtain a reaction product containing 95% diphenylhexamethylcyclotetrasiloxane, the major impurity being diphenyltetramethylcyclotrisiloxane. After distillation to separate the trimer, the reaction product containing about 50% 2,6-cis-diphenylhexamethylcyclotetrasiloxane and about 50% of the 2,6-trans isomer was fractionally crystallized to obtain a mixture of 67% 2,6-cis and 37% 2,6-trans. Fractional distillation of this mixture resulted in an enriched product containing about 80% of the 2,6-cis isomer. The enriched product was then subjected to a second fractional crystallization to obtain a product containing 99.23% 2,6-cis-diphenylhexamethylcyclotetrasiloxane and 0.74% of 2,6-trans isomer; the remainder being a mixture of the 2,4-cis and trans isomers. The product purity was determined by both g.l.c. and H'NMR analysis.

That which is claimed is:

1. A method of producing palliative action in the treatment of prostate carcinoma comprising administering to a patient suffering from said disease an amount effective to provide palliative relief of 2,6-cis-diphenylhexamethylcyclotetrasiloxane.

2. A method in accordance with claim 1 wherein the 2,6-cis-diphenylhexamethylcyclotetrasiloxane is administered orally.

3. A method in accordance with claim 2 wherein the siloxane is administered in combination with a pharmaceutically acceptable carrier.

4. A method in accordance with claim 3 wherein the carrier is selected from the group consisting of sesame oil, soya oil, corn oil and oleic acid.

5. A method in accordance with claim 1 wherein a daily dosage in the range of 1 to 50 mg./kg. body weight of said siloxane is administered to said patient.

* * * * *